(12) United States Patent
Kim et al.

(10) Patent No.: US 7,396,624 B2
(45) Date of Patent: *Jul. 8, 2008

(54) ELECTROPHOTOGRAPHIC PHOTORECEPTOR CONTAINING NAPHTHALENETETRACARBOXYLIC ACID DIIMIDE DERIVATIVES AND ELECTROPHOTOGRAPHIC IMAGING APPARATUS EMPLOYING THE SAME

(75) Inventors: Beom-jun Kim, Seongnam-si (KR); Seung-ju Kim, Suwon-si (KR); Saburo Yokota, Suwon-si (KR); Kyung-yol Yon, Seongnam-si (KR); Hwan-koo Lee, Suwon-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 356 days.

This patent is subject to a terminal disclaimer.

(21) Appl. No.: 11/095,522

(22) Filed: Apr. 1, 2005

(65) Prior Publication Data
US 2005/0227156 A1   Oct. 13, 2005

(30) Foreign Application Priority Data
Apr. 9, 2004   (KR) ............... 10-2004-0024503

(51) Int. Cl.
*G03G 5/06* (2006.01)
(52) U.S. Cl. ..................... 430/78; 399/159
(58) Field of Classification Search ............ 430/78; 399/159
See application file for complete search history.

(56) References Cited

U.S. PATENT DOCUMENTS

| 4,992,349 | A | 2/1991 | Chen et al. |
| 5,019,473 | A | 5/1991 | Nguyen et al. |
| 5,468,583 | A | 11/1995 | Gruenbaum et al. |
| 6,174,638 | B1 | 1/2001 | Ishigami et al. |
| 6,656,650 | B1 | 12/2003 | Lin et al. |
| 2005/0019685 | A1 | 1/2005 | Kim et al. |
| 2005/0130051 | A1 | 6/2005 | Kim et al. |

FOREIGN PATENT DOCUMENTS

| DE | 1 228 267 | | 11/1966 |
| EP | 1340755 | A1 * | 9/2003 |
| GB | 1172715 | | 12/1969 |
| JP | 5-25174 | | 2/1993 |
| JP | 2003-327587 | | 11/2003 |

OTHER PUBLICATIONS

Todd et al., "Chiral imides as potential chiroptical switches: synthesis and optical properties", Tetrahedron Letters, vol. 46, No. 4, Jan. 24, 2005, pp. 587-590.
Gawronski et al., "Chiral C and S Conformers of Aromatic Diimide Triads", Chirality, vol. 13, No. 6, May 16, 2001, pp. 322-328.
Borsenberger et al., Electron Trapping in N,N'-bis(1,2-dimethylpropyl)-1,4,5,8-Naphthalenetetracarboxylic Diimide Doped Poly(styrene), Journal of Imaging Science and Technology, vol. 43, No. 3, May 1999, pp. 201-205.
Gawronski, J., Chiral C and S Conformers of Aromatic Diimide Triads, Chirality 13:322-328 (2001).

* cited by examiner

*Primary Examiner*—Christopher RoDee
(74) *Attorney, Agent, or Firm*—Roylance, Abrams, Berdo & Goodman, L.L.P.

(57) ABSTRACT

An electrophotographic photoreceptor containing a naphthalenetetracarboxylic acid diimide derivative of Formula (1), which has a branched alkyl group substituted with an aryl group at the α-position with regard to nitrogen atoms of imide groups:

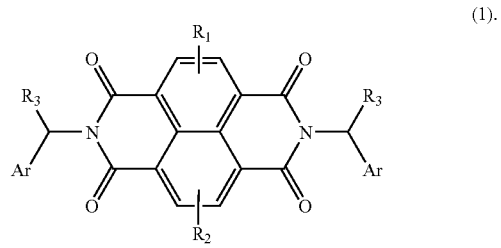

(1).

wherein $R_1$ and $R_2$ are independently selected from the group consisting of a hydrogen atom, a halogen atom, a $C_1$-$C_{20}$ substituted or unsubstituted alkyl group, and a $C_1$-$C_{20}$ substituted or unsubstituted alkoxy group;

$R_3$ is selected from the group consisting of a $C_1$-$C_{20}$ substituted or unsubstituted alkyl group, a $C_1$-$C_{20}$ substituted or unsubstituted alkoxy group, a $C_7$-$C_{30}$ substituted or unsubstituted aralkyl group, and a group having the formula —$(CH_2)_n$—Y—$R_4$;

Ar is a $C_6$-$C_{30}$ substituted or unsubstituted aryl group;

Y is an oxygen or sulfur atom;

$R_4$ is a hydrogen atom or a $C_1$-$C_{20}$ substituted or unsubstituted alkyl group; and n is an integer between 1 and 12.

The naphthalenetetracarboxylic acid diimide derivative has high solubility in organic solvents and compatibility with binder resins, thus providing better electron transporting ability. The invention is also directed to an electrophotographic imaging apparatus using the photoreceptor.

9 Claims, 2 Drawing Sheets

ELECTROPHOTOGRAPHIC PHOTORECEPTOR CONTAINING NAPHTHALENETETRACARBOXYLIC ACID DIIMIDE DERIVATIVES AND ELECTROPHOTOGRAPHIC IMAGING APPARATUS EMPLOYING THE SAME

BACKGROUND OF THE INVENTION

This application claims the benefit under 35 U.S.C. § 119 of Korean Patent Application No. 10-2004-0024503, filed on Apr. 9, 2004, in the Korean Intellectual Property Office, the disclosure of which is hereby incorporated by reference in its entirety.

1. Field of the Invention

The present invention relates to an electrophotographic photoreceptor and an electrophotographic imaging apparatus employing the photoreceptor. More particularly, the invention is directed to an electrophotographic photoreceptor containing a naphthalenetetracarboxylic acid diimide derivative having high solubility in organic solvents and strong compatibility with polymer binder resins to provide strong electron transporting ability. The invention is further directed to an electrophotographic imaging apparatus employing the naphthalenetetracarboxylic acid diimide derivative.

2. Description of the Related Art

In electrophotography that is used in laser printers, photocopiers, CRT printers, LED printers, liquid crystal printers etc., an electrophotographic photoreceptor in the form of a plate, disk, sheet, belt, drum or the like includes an photosensitive layer formed on an electrically conductive substrate. In electrophotography, the electrophotographic photoreceptor is imaged by first uniformly electrostatically charging the surface of the photosensitive layer, and then exposing the charged surface to a pattern of light. The light exposure selectively dissipates the charge in the illuminated areas where light strikes the surface, thereby forming a pattern of charged and uncharged areas, referred to as a latent image. A liquid or solid toner is then provided in the vicinity of the latent image, and toner droplets or particles deposit in the vicinity of either the charged or uncharged areas to create a toned image on the surface of the photosensitive layer. The resulting toned image can be transferred and fixed to a suitable ultimate or intermediate receiving surface, such as paper, thereby completing the formation of an image. The residual toner is then cleaned and residual charges are erased from the electrophotographic photoreceptor. Thus, the electrophotographic photoreceptor can be repeatedly used for long periods of time.

The electrophotographic photoreceptor includes an inorganic photoreceptor in which an inorganic material such as selenium or amorphous silicon is used in a photosensitive layer, and an organic photoreceptor in which an organic material is used in a photosensitive layer. The organic photoreceptor can be easily manufactured. A charge generating material (CGM), a charge transporting material (CTM), and a binder resin can be selected from a wide variety of respective candidate materials to provide a high degree of freedom in designing the photoreceptor.

Electrophotographic photoreceptors are widely categorized into two types. The first is a laminated-type having a laminated structure including a charge generating layer comprising a binder resin and a CGM, and a charge transporting layer comprising a binder resin and a CTM (mainly a hole transporting material (HTM)). In general, the laminated-type electrophotographic photoreceptor is used in the fabrication of a negative (−) type electrophotographic photoreceptor in which the charge generating layer and the charge transporting layer are sequentially laminated on the electrically conductive substrate. The second type is a single layer type in which a binder resin, a CGM, a HTM and an electron transporting material (ETM) are dispersed in an electophotosensitive layer. In general, the single layer-type organic photoreceptor is used in the fabrication of a positive (+) type electrophotographic photoreceptor.

The (+) type single layered electrophotographic photoreceptor has the advantage in that it generates a small amount of ozone that is harmful to humans. In addition, the (+) type single layered photoreceptor has a single photosensitive layer so that the production costs are low. The most essential material among the materials in the (+) type single layered electrophotographic photoreceptor is the ETM. Since the hole transporting ability of the HTM is 100 times greater than the electron transporting ability of the commonly used ETM, the performance of the single layered electrophotographic photoreceptor is dependent upon the electron transporting ability of the ETM.

The electron transporting ability of the ETM is considerably influenced by the solubility in organic solvents and the compatibility with polymer binder resins of the photosensitive layer. Widely known conventional ETMs include dicyanofluorenone derivatives having the formula (i) below and naphthalenetetracarboxylic acid diimide derivatives having the formula (ii) below.

(i)

in which $R_3'$ is a substituted or unsubstituted alkyl or aryl group.

(ii)

in which $R_1'$ and $R_2'$ are independently a substituted or unsubstituted alkyl group, or a substituted or unsubstituted cyclic alkyl group.

However, dicyanofluorenone derivatives have low solubility in organic solvents and poor electron transporting ability. Thus, when fabricating an electrophotographic photoreceptor using these materials as the ETM, the electrophotographic photoreceptor has disadvantages such as a reduced charging potential and an increased exposure potential after long periods of repeated use. Meanwhile, it is known that the naphthalenetetracarboxylic acid diimide derivatives disclosed in U.S. Pat. Nos. 4,992,349 and 5,468,583 exhibit an electron transporting ability better than naphthoquinone derivatives, which have been conventionally used as the ETM. U.S. Pat. Nos. 4,992,349 and 5,468,583 are hereby incorporated by refer- ence in their entirety. However, the naphthalenetetracarboxylic acid diimide derivatives have low solubility in organic solvents and poor compatibility with polymer binder resins, and thus still have a poor electron transporting ability. Thus, when fabricating an electrophotographic photoreceptor, in particular, a single layered electrophotographic photoreceptor, using these materials as the ETM, the electrophotographic photoreceptor has problems such as a reduced charging potential and an increased exposure potential after long periods of repeated use.

SUMMARY OF THE INVENTION

The present invention provides an electrophotographic photoreceptor containing the new naphthalenetetracarboxylic acid diimide derivative having high solubility in organic solvents and strong compatibility with polymer binder resins, thereby providing better electron transporting ability.

The present invention also provides an electrophotographic imaging apparatus, an electrophotographic cartridge, and an electrophotographic photoreceptor drum employing the electrophotographic photoreceptor.

According to an aspect of the present invention, there is provided an electrophotographic photoreceptor including an electrically conductive substrate and a photosensitive layer formed thereon The photosensitive layer includes a naphthalenetetracarboxylic acid diimide derivative of Formula (1) below:

where $R_1$ and $R_2$ are independently selected from the group consisting of a hydrogen atom, a halogen atom, a $C_1$-$C_{20}$ substituted or unsubstituted alkyl group, and a $C_1$-$C_{20}$ substituted or unsubstituted alkoxy group;

$R_3$ is selected from the group consisting of a $C_1$-$C_{20}$ substituted or unsubstituted alkyl group, a $C_1$-$C_{20}$ substituted or unsubstituted alkoxy group, a $C_7$-$C_{30}$ substituted or unsubstituted aralkyl group, and a group having the formula —(CH$_2$)$_n$—Y—R$_4$;

Ar is a $C_6$-$C_{30}$ substituted or unsubstituted aryl group;

Y is an oxygen or sulfur atom;

$R_4$ is a hydrogen atom or a $C_1$-$C_{20}$ substituted or unsubstituted alkyl group; and n is an integer between 1 and 12.

According to another aspect of the present invention, there is provided an electrophotographic imaging apparatus including an electrophotographic photoreceptor, wherein the electrophotographic photoreceptor includes an electrically conductive substrate and a photosensitive layer formed thereon, the photosensitive layer including a naphthalenetetracarboxylic acid diimide derivative having Formula (1) above.

According to another aspect of the present invention, there is provided an electrophotographic cartridge including: an electrophotographic photoreceptor including an electrically conductive substrate and a photosensitive layer formed thereon, the photosensitive layer including a naphthalenetetracarboxylic acid diimide derivative of Formula (1) above; and at least one of a charging device for charging the electrophotographic photoreceptor, a developing device for developing an electrostatic latent image formed on the electrophotographic photoreceptor, and a cleaning device for cleaning a surface of the electrophotographic photoreceptor, wherein, the electrophotographic cartridge is attachable to or detachable from an image forming apparatus.

According to another aspect of the present invention, there is provided an electrophotographic photoreceptor drum including: a drum attachable to and detachable from an image forming apparatus; and an electrophotographic photoreceptor disposed on the drum, wherein the electrophotographic photoreceptor includes an electrically conductive substrate and a photosensitive layer formed thereon, the photosensitive layer including a naphthalenetetracarboxylic acid diimide derivative of Formula (1) above.

According to another aspect of the present invention, there is provided an image forming apparatus including: a photoreceptor unit including an electrically conductive substrate and a photosensitive layer formed thereon, the photosensitive layer including a naphthalenetetracarboxylic acid diimide derivative of Formula (1) above; a charging device charging the photoreceptor unit; an image-forming light irradiating device irradiating light onto the charged photoreceptor unit to form an electrostatic latent image on the photoreceptor unit; a developing unit developing the electrostatic latent image with a toner to form a toner image on the photoreceptor unit; and a transfer device transferring the toner image onto a receiving material.

The naphthalenetetracarboxylic acid diimide derivatives of Formula (1) above and having branched alkyl groups substituted with aryl groups at α-position, has higher solubility in organic solvents and better compatibility with polymer binder resins compared to that of the conventional naphthalenetetracarboxylic acid diimide derivatives. Thus, when fabricating an electrophotographic photoreceptor using these compounds as the ETM, the electron transporting ability in a photosensitive layer is improved. Therefore, these compounds can be effectively used even in the fabrication of a single layered electrophotographic photoreceptor.

These and other aspects of the invention will become apparent from the following detailed description of the invention, which in conjunction with the annexed drawings disclose various embodiments of the invention.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

An electrophotographic photoreceptor and an electrophotographic imaging apparatus employing the photoreceptor according to the present invention will now be described in more detail.

The naphthalenetetracarboxylic acid diimide derivatives according to the present invention include branched alkyl groups substituted with aryl groups at the α-position bonded to the nitrogen of each imide group. The derivatives of the invention have higher solubility in organic solvents and better compatibility with polymer binder resins when compared to conventional naphthalenetetracarboxylic acid diimide compounds substituted with an alkyl group at the α-position, thus providing improved electron transporting ability. The naphthalenetetracarboxylic acid diimide derivatives of the invention have the Formula (1):

(1)

where $R_1$ and $R_2$ are independently selected from the group consisting of a hydrogen atom, a halogen atom, a $C_1$-$C_{20}$ substituted or unsubstituted alkyl group, and a $C_1$-$C_{20}$ substituted or unsubstituted alkoxy group;

$R_3$ is selected from the group consisting of a $C_1$-$C_{20}$ substituted or unsubstituted alkyl group, a $C_1$-$C_{20}$ substituted or unsubstituted alkoxy group, a $C_7$-$C_{30}$ substituted or unsubstituted aralkyl group, and a group having the formula —$(CH_2)_n$—Y—$R_4$;

Ar is a $C_6$-$C_{30}$ substituted or unsubstituted aryl group;
Y is an oxygen or sulfur atom;
$R_4$ is a hydrogen atom or a $C_1$-$C_{20}$ substituted or unsubstituted alkyl group; and
n is an integer between 1 and 12.

In Formula (1), the halogen atom is selected from the group consisting of fluorine, chlorine, bromine, and iodine.

In Formula (1), the alkyl group of $R_1$, $R_2$, and $R_3$ is a $C_1$-$C_{20}$, preferably a $C_1$-$C_{12}$, linear or branched alkyl group. Examples of the alkyl group include methyl, ethyl, n-propyl, isopropyl, n-butyl, isobutyl, sec-butyl, tert-butyl, pentyl, hexyl, 1,2-dimethylpropyl, 2-ethylhexyl, and the like. The alkyl group may be substituted with a halogen atom, for example, fluorine, chlorine, bromine or iodine.

In Formula (1), the alkoxy group of $R_1$, $R_2$ and $R_3$ is a $C_1$-$C_{20}$, preferably a $C_1$-$C_{12}$, linear or branched alkoxy group. Examples of the alkoxy group include methoxy, ethoxy, propoxy, and the like. The alkoxy group may be substituted with a halogen atom, for example, fluorine, chlorine, bromine or iodine.

In Formula (1), the aralkyl group of $R_3$ is a $C_7$-$C_{30}$, preferably a $C_7$-$C_{15}$, linear or branched aralkyl group. Examples of the aralkyl group include benzyl, methylbenzyl, phenylethyl, naphthylmethyl, naphthylethyl, and the like. The aralkyl group may be substituted with a halogen atom, for example, fluorine, chlorine, bromine or iodine, an alkyl group, an alkoxy group, a nitro group, a hydroxy group, sulfonic acid group, and the like.

In Formula (1), $R_3$ may be a group having the formula —$(CH_2)_n$—Y—$R_4$. Y is an oxygen or sulfur atom, n is an integer between 1 and 12, and $R_4$ is a hydrogen atom or a $C_1$-$C_{20}$ substituted or unsubstituted alkyl group. Examples of the group include hydroxymethyl, hydroxyethyl, —$CH_2$—S—$CH_3$, and the like.

In Formula (1), the aryl group represented by Ar is a $C_6$-$C_{30}$ aromatic ring. Examples of the aryl group include phenyl, tolyl, xylyl, biphenyl, o-terphenyl, naphthyl, anthracenyl, phenenthrenyl, and the like. The aryl group may be substituted with an alkyl group, an alkoxy group, a nitro group, hydroxy group, sulfonic acid group or a halogen atom.

In one preferred embodiment, the derivative of Formula (1) is bisymetrical where each $R_3$ and Ar are the same.

Examples of naphthalenetetracarboxylic acid diimide derivatives of Formula (1) include:

Compound (1)

Compound (2)

Compound (3)

Compound (4)

Compound (5)

Compound (6)

Compound (7)

X = F, Cl, Br, or I

Compound (8)

Compound (9)

Compound (10)

Compound (11)

Compound (12)

Compound (13)

Compound (14)

Compound (15)

In one embodiment, the naphthalenetetracarboxylic acid diimide derivative of Formula (1) is wherein $R_1$ and $R_2$ are a hydrogen atom, $R_3$ is selected from the group consisting of methyl, ethyl, propyl, butyl, pentyl, benzyl, or methylbenzyl, and Ar is selected from the group consisting of phenyl, nitrophenyl, hydroxyphenyl, halophenyl, methoxyphenyl, methylphenyl, naphthyl, anthracenyl, and phenanthrenyl.

The examples of naphthalenetetracarboxylic acid diimide derivatives are identified in the following Table:

| Compound | $R_1$, $R_2$ | $R_3$ | Ar |
|---|---|---|---|
| 1 | H | —$CH_3$ | phenyl(—$C_6H_5$) |
| 2 | H | —$CH_2CH_3$ | phenyl(—$C_6H_5$) |
| 3 | H | —$CH_2CH_2OH$ | phenyl(—$C_6H_5$) |
| 4 | H | —$CH_2CH_2CH_2OH$ | phenyl(—$C_6H_5$) |
| 5 | H | —$CH_3$ | nitrophenyl(—$C_6H_4NO_2$) |
| 6 | H | —$CH_3$ | hydroxyphenyl(—$C_6H_4OH$) |
| 7 | H | —$CH_3$ | halophenyl(—$C_6H_5X$) |
| 8 | H | benzyl (—$CH_2C_6H_5$) | phenyl(—$C_6H_5$) |
| 9 | H | methyl benzyl | phenyl(—$C_6H_5$) |
| 10 | H | —$CH_3$ | 2-naphthyl(—$C_{10}H_7$) |
| 11 | H | —$CH_3$ | 3-naphthyl(—$C_{10}H_7$) |
| 12 | H | —$CH_3$ | methoxyphenyl(—$C_6H_4OCH_3$) |
| 13 | H | —$CH_3$ | methylphenyl(—$C_6H_4CH_3$) |
| 14 | H | —$CH_2SCH_3$ | phenyl(—$C_6H_5$) |
| 15 | H | tert butyl(—$C(CH_3)_3$) | phenyl(—$C_6H_5$) |

In one embodiment of the invention, the naphthalenetetracarboxylic acid diimide of Formula (1) is where $R_1$, $R_2$ are H, Ar is phenyl and $R_3$ is selected from the group consisting of $CH_3$, $CH_2CH_3$, $CH_2CH_2OH$, $CH_2CH_2CH_2OH$, benzyl, methyl benzyl, $CH_2SCH_3$ and tertbutyl. In another embodiment, the naphthalenetetracarboxylic acid diimides of Formula (1) are where $R_1$, $R_2$ are H, $R_3$ is methyl and Ar is selected from the group consisting of phenyl, hydroxyphenyl, nitrophenyl, halophenyl, 2-naphthyl, 3-naphthyl, methoxyphenyl and methylphenyl.

The naphthalenetetracarboxylic acid diimide derivatives of the present invention is prepared by reacting a naphthalenetetracarboxylic acid dianhydride (2a) with a secondary amine (3a) below:

In this reaction, an organic solvent, for example, dimethylformamide (DMF), dimethylacetamide (DMAc), hexamethylphosphoramide (HMPA), or N-methylpyrrolidone (NMP), may be used. The reaction temperature may be set in the range of 20° C. below the boiling point of the solvent up to the boiling point of the solvent, and preferably, in the range of 10° C. below the boiling point of the solvent up to the boiling point of the solvent.

Typically, the reaction may be carried out as follows. The naphthalenetetracarboxylic acid dianhydride is dissolved in an organic solvent, for example, DMF, DMAc, HMPA, or NMP, and then the secondary amine is added dropwise. Then, the mixture is heated to the boiling point of the solvent and refluxed for 3 to 10 hours to obtain the naphthalenetetracarboxylic acid diimide derivative. In this case, the naphthalenetetracarboxylic acid dianhydride and the secondary amine may be used in a molar ratio of 1:2. When the secondary amine is used in excess, the purification of the resulting reaction product may be difficult.

An electrophotographic imaging apparatus, an electrophotographic photoreceptor drum, and an electrophotographic cartridge employing the electrophotographic photoreceptor including the naphthalenetetracarboxylic acid diimide derivative having Formula (1) will now be described in detail.

Figure 1:
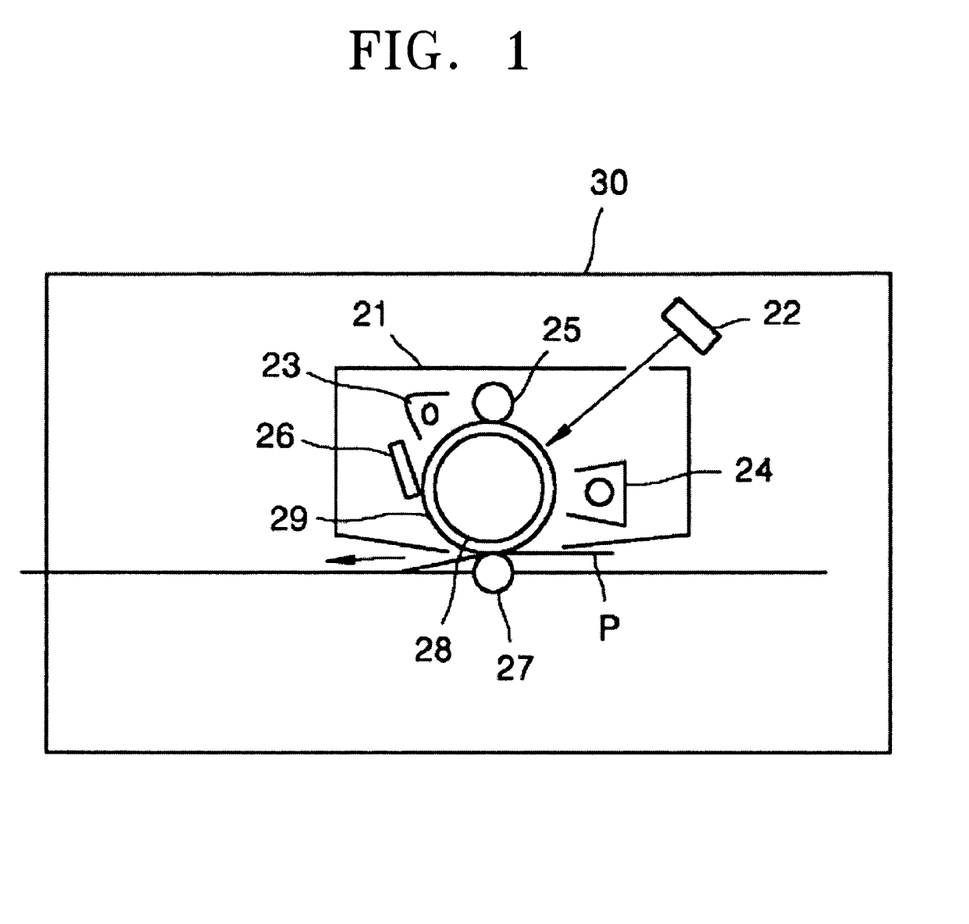
FIG. 1 schematically illustrates an image forming apparatus, an electrophotographic photoreceptor drum, and an electrophotographic cartridge according to an embodiment of the present invention.

FIG. 1 schematically illustrates an image forming apparatus 30 including an electrophotographic photoreceptor drum 28, 29 and an electrophotographic cartridge 21 according to an embodiment of the present invention. The electrophotographic cartridge 21 typically includes an electrophotographic photoreceptor 29, one or more charging devices 25 charging the electrophotographic photoreceptor 29, a developing device 24 developing an electrostatic latent image formed on the electrophotographic photoreceptor 29, and a cleaning device 26 for cleaning a surface of the electrophotographic photoreceptor 29. The electrophotographic cartridge 21 can be attached to and detached from the image forming apparatus 30.

The electrophotographic photoreceptor drum 28, 29 of the image forming apparatus 30 can generally be attached to and detached from the image forming apparatus 30 and includes the drum 28 on which the electrophotographic photoreceptor 29 is placed.

Generally, the image forming apparatus 30 includes a photosensitive unit (for example, the drum 28 and the electrophotographic photoreceptor 29); the charging device 25 for charging the photoreceptor unit; an image-forming light irradiating device 22 for irradiating light onto the charged photoreceptor unit to form an electrostatic latent image on the photoreceptor unit; the developing unit 24 for developing the electrostatic latent image with a toner to form a toner image on the photoreceptor unit; and a transfer device 27 for transferring the toner image onto a receiving material, such as paper P. The photosensitive unit includes the electrophotographic photoreceptor 29, which will be described below. The charging device 25 may be supplied with a voltage as a charging unit and may charge the electrophotographic photoreceptor 29. The image forming apparatus 30 may also include a pre-exposure unit 23 to erase a residual charge on the surface of the electrophotographic photoreceptor 29 to prepare for a next cycle.

The photoreceptor including the naphthalenetetracarboxylic acid diimide derivative of Formula (1) according to the present invention can be incorporated into electrophotographic imaging apparatuses, such as laser printers, photocopiers, and facsimile machines.

Hereinafter, an electrophotographic photoreceptor including the naphthalenetetracarboxylic acid diimide derivative of Formula (1), which is employed in the electrophotographic imaging apparatus according to the present invention, will be described in detail.

In the electrophotographic photoreceptor, a photosensitive layer is formed on an electrically conductive substrate. The electrically conductive substrate is in the form of a drum- or belt-shaped substrate made of, for example, a metal or an electroconductive polymer. Examples of the metal include aluminum, stainless steel, and the like. Examples of the electroconductive polymer include polyester resins, polycarbonate resins, polyamide resins, polyimide resins, and copolymers thereof in which an electroconductive material, such as electroconductive carbon, tin oxide, indium oxide, is dispersed.

The photosensitive layer may be a laminated type where a charge generating layer and a charge transport layer are separately formed, or a single layered type where a layer acts as both a charge generating layer and a charge transport layer.

The naphthalenetetracarboxylic acid diimide derivative of Formula (1) according to the present invention acts as the charge transport material, and preferably, the electron transport material (ETM). In the laminated type photosensitive layer, the naphthalenetetracarboxylic acid diimide derivative of Formula (1) is contained in the charge transport layer, and in the single layered type photosensitive layer, it is naturally contained in a single layer together with the charge generating material (CGM).

Examples of the CGM used for the photosensitive layer include organic materials such as phthalocyanine pigments, azo pigments, quinone pigments, perylene pigments, indigo pigments, bisbenzoimidazole pigments, quinacridone pigments, azulenium dyes, squarylium dyes, pyrylium dyes, triarylmethane dyes, and cyanine dyes, and inorganic materials such as amorphous silicon, amorphous selenium, trigonal selenium, tellurium, selenium-tellurium alloy, cadmium sulfide, antimony sulfide, and zinc sulfide. The CGM is not limited to the materials listed herein, and may be used alone or in a combination of two or more.

In case of the laminated type photoreceptor, the CGM is dispersed in a solvent with a binder resin and then the dispersion is coated on the electrically conductive substrate using a dip coating, a ring coating, a roll coating, or a spray coating method to form the charge generating layer. The thickness of the charge generating layer is generally in the range of 0.1 to 1.0 μm. When the thickness is less than 0.1 μm, the sensitivity is insufficient, and when the thickness is greater than 1 μm, the charging ability and the sensitivity are lowered.

A charge transport layer containing the naphthalenetetracarboxylic acid diimide derivative of Formula (1) is formed on the charge generating layer of the laminated type photosensitive layer, but the charge generating layer may be formed on the charge transport layer in reverse order. When forming the charge transport layer, the naphthalenetetracarboxylic acid diimide derivative of Formula (1) and the binder resin are dissolved in a solvent and the resulting solution is coated on the charge generating layer. Examples of the coating method include a dip coating, a ring coating, a roll coating, and a spray coating method, similar to the methods used to form charge generating layer. The thickness of the charge transport layer may be in the range of about 5-50 μm. When the thickness is less than 5 μm, the charging ability becomes poor, and when the thickness is greater than 50 μm, the response rate is reduced and the image quality is deteriorated.

When preparing the single layered photoreceptor, the CGM is dispersed in a solvent together with the binder resin and the charge transport material and the resulting dispersion is coated on the electrically conductive substrate to obtain the photosensitive layer. The thickness of the photosensitive layer may be typically in the range of about 5-50 μm. In this case, the naphthalenetetracarboxylic acid diimide derivative of Formula (1) is used as a charge transport material, but may be used together with other charge transport materials. Although the charge transport material includes a hole transport material (HTM) and an ETM, it is preferable to use the HTM together with the naphthalenetetracarboxylic acid diimide derivative of Formula (1) in the single layered photoreceptor.

Examples of the HTM that may be used with the naphthalenetetracarboxylic acid diimide derivative of Formula (1) in the photosensitive layer include nitrogen containing cyclic compounds or condensed polycyclic compounds such as pyrene compounds, carbazole compounds, hydrazone compounds, oxazole compounds, oxadiazole compounds, pyrazoline compounds, arylamine compounds, arylmethane compounds, benzidine compounds, thiazole compounds or styryl compounds. Also, high molecular weight compounds or polysilane compounds having functional groups of the above compounds on a backbone or side chain may be used.

Examples of other ETM that may be used with the naphthalenetetracarboxylic acid diimide derivative of Formula (1) in the photosensitive layer include, but are not limited to, electron attracting low-molecular weight compounds such as benzoquinone compounds, cyanoethylene compounds, cyanoquinodimethane compounds, fluorenone compounds, xanthone compounds, phenanthraquinone compounds, anhydrous phthalic acid compounds, thiopyrane compounds, or diphenoquinone compounds. Electron transporting polymer compounds or pigments having n-type semiconductor characteristic may also be used.

The ETM or the HTM that may be used with the naphthalenetetracarboxylic acid diimide derivative of Formula (1) in the electrophotographic photoreceptor are not limited to the materials listed herein, and the foregoing materials may be used alone or in combination of two or more.

Examples of solvents used in the formation of coating composition for forming the photosensitive layer include organic solvents such as alcohols, ketones, amides, ethers, esters, sulfones, aromatics, halogenated aliphatic hydrocarbons, and the like. The coating method of the coating composition for forming the photosensitive layer may be a dip coating method, but a ring coating, a roll coating, a spray coating method and the like may be also used.

Examples of the binder resin used in the formation of the photosensitive layer include, but are not limited to, polycarbonate, polyester, methacrylic resin, acrylic resin, polyvinyl chloride, polyvinylidene chloride, polystyrene, polyvinyl acetate, silicon resin, silicon-alkyd resin, styrene-alkyd resin, poly-N-vinylcarbazole, phenoxy resin, epoxy resin, polyvinyl butyral, polyvinyl acetal, polyvinyl formal, polysulfone, polyvinyl alcohol, ethyl cellulose, phenolic resin, polyamide, carboxy-methyl cellulose and polyurethane. These polymers may be used alone or in a combination of two or more.

The amount of the charge transport material including the ETM and the HTM in the photoconductive layer may be in the range of 10-60% by weight based on the total weight of the photosensitive layer. If the amount is less than 10% by weight, the sensitivity is insufficient due to low charge transporting ability, thereby resulting in an increased residual potential. If the amount is more than 60% by weight, the amount of the resin in the photosensitive layer is reduced, thereby resulting in a reduced mechanical strength.

In the present invention, an electroconductive layer may further be formed between the electrically conductive substrate and the photosensitive layer. The electroconductive layer is obtained by dispersing an electroconductive powder such as carbon black, graphite, metal powder or metal oxide powder in a solvent and then applying the resulting dispersion on the electrically conductive substrate and drying it. The thickness of the electroconductive layer may be in the range of about 5 to about 50 μm.

Further, an intermediate layer may be interposed between the electrically conductive substrate and the photosensitive layer or between the electroconductive layer and the photosensitive layer to enhance adhesion or to prevent charges from being injected from the substrate. Examples of the intermediate layer include, but are not limited to, an aluminum anodized layer; a resin-dispersed layer of metal oxide powder such as titanium oxide or tin oxide; and a resin layer such as polyvinyl alcohol, casein, ethylcellulose, gelatin, phenol resin, or polyamide. The thickness of the intermediate layer may be in the range of 0.05 to 5 μm.

Also, the photosensitive layer may contain a plasticizer, a leveling agent, a dispersion stabilizing agent, an antioxidant or a photo-stabilizing agent, in addition to the binder resin.

Examples of the antioxidant include hindered phenol compounds, sulfur compounds, phosphorus compounds, and amine compounds. Examples of the photo-stabilizing agent include benzotriazole compounds, benzophenone compounds, and hindered amine compounds.

Also, the electrophotographic photoreceptor of the present invention may further include a surface protecting layer, as may be necessary in some embodiments.

The present invention will now be described in greater detail with reference to the following examples. The following examples are for illustrative purposes and are not intended to limit the scope of the invention.

EXAMPLES

Synthesis Example 1

Synthesis of Compound (1)

The following is a description of the synthesis of the compound (1) having the formula below.

Compound (1)

Figure 2:
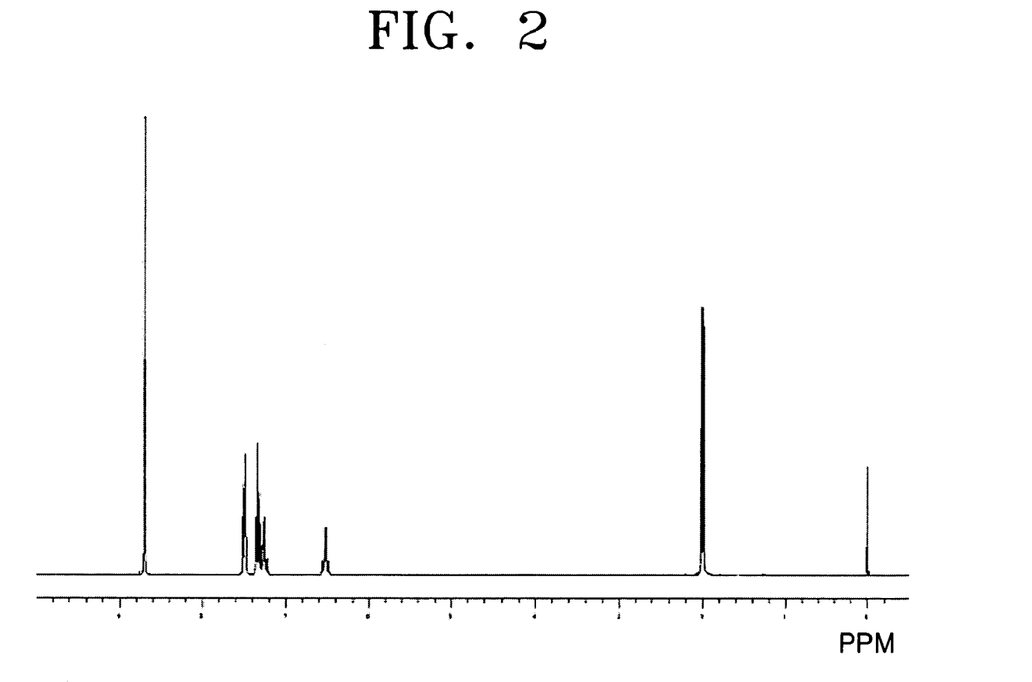
FIG. 2 is an NMR spectrum of a naphthalenetetracarboxylic acid diimide derivative Compound (1) obtained in Synthesis Example 1 of the present invention.

A 250 ml three neck flask equipped with a reflux condenser was purged with nitrogen, and then 10.72 g (0.04 mol) of 1,4,5,8-naphthalenetetracarboxylic dianhydride and 100 ml of DMF were added and stirred at room temperature. Then, a solution of 9.7 g (0.08 mol) of α-methylbenzylamine in 20 ml of DMF was added dropwise and stirred at room temperature for 1 hour. The mixture was heated and then refluxed for 3 hours, and cooled to room temperature. 60 ml of methanol was added to the mixture and the resulting product was precipitated and filtered. The filtered product was recrystallized from a chloroform/ethanol solvent and dried in a vacuum oven to obtain 15.37 g of a white crystal (yield: 81%). The NMR spectrum of the obtained Compound (1) is shown in FIG. 2.

Synthesis Example 2

Synthesis of Compound (2)

The following is a description of the synthesis of the compound (2) having the formula below.

Compound (2)

Figure 3:
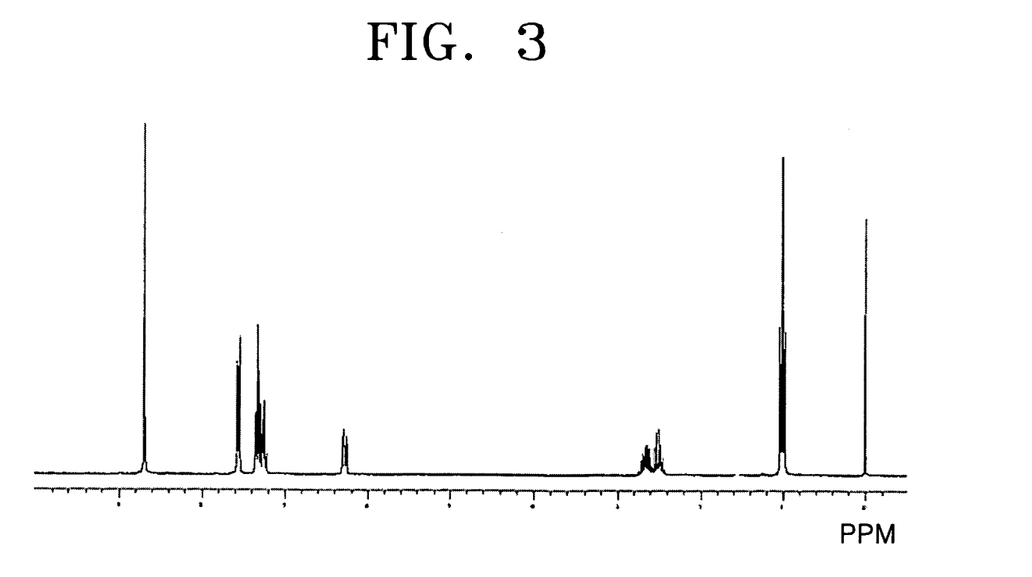
FIG. 3 is an NMR spectrum of a naphthalenetetracarboxylic acid diimide derivative Compound (2) obtained in Synthesis Example 2 of the present invention.

15.86 g of the Compound (2) was obtained as a white crystal in the same manner as in Synthesis Example 1, except that 10.82 g (0.08 mol) of 1-phenylpropylamine was used instead of α-methylbenzylamine (yield: 79%). The NMR spectrum of the obtained Compound (2) is shown in FIG. 3.

Solubility Test

1 g of the compound to be tested was added to a test tube at room temperature and methylene chloride was added dropwise while stirring to determine the amount of methylene chloride required to completely dissolve 1 g of the test compound. The test results are shown in Table 1.

TABLE 1

| | Amount of methylene chloride required to dissolve 1 g of a compound (g) |
|---|---|
| Compound (1) | 3.5 |
| Compound (2) | 2 |
| Comparative Compound (9a)*1 | 25 |
| Comparative Compound (10a)*2 | 17.5 |

*1: naphthalenetetracarboxylic acid diimide derivative of Compound (9a) as used in Comparative Example 2
*2: naphthalenetetracarboxylic acid diimide derivative of Compound (10a) as used in Comparative Example 3

(4a)

Referring to Table 1, 25 g of methylene chloride was required to dissolve 1 g of the comparative Compound (9a), whereas only 3.5 g of methylene chloride was required to dissolve 1 g of the Compound (1) having a phenyl group instead of a methyl group of the comparative Compound (9a). The solubility test results of the Compound (2) and the comparative Compound (10a) are similar to those of Compound (1) and the comparative Compound (9a). 17.5 g of methylene chloride was used to dissolve 1 g of the comparative Compound (10a), whereas only 2 g of methylene chloride was used to dissolve 1 g of the Compound (2) having a phenyl group instead of an ethyl group of the comparative Compound (10a). As seen from the results, the naphthalenetetracarboxylic acid diimide derivative having a branched alkyl substituted with an aryl group at a-position on the alkyl group according to the present invention has a solubility in organic solvents that is higher than the naphthalenetetracarboxylic acid diimide derivative having a branched alkyl substituted with an alkyl group at α-position.

Example 1

29.7 parts by weight of the Compound (1) as an ETM, 3 parts by weight of x-type metal free phthalocyanine Compound (4a) below, 14.9 parts by weight of an enaminestilben-based HTM of Compound (5a) below, 52.4 parts by weight of a binder resin (O-PET, available from KANEBO) of Compound (6a), 280 parts by weight of methylene chloride, and 120 parts by weight of 1,1,2-trichloroethane were sand milled for 2 hours and ultrasonically dispersed. The obtained solution was coated on an anodized aluminum drum using a ring bar and dried at 110° C. for 1 hour to prepare an electrophotographic photoreceptor drum having a thickness of about 15 to 16 μm.

(5a)

(6a)

Example 2

An electrophotographic photoreceptor drum was prepared in the same manner as in Example 1, except that 29.7 parts by weight of the Compound (2) was used as the ETM instead of the Compound (1).

Example 3

An electrophotographic photoreceptor drum was prepared in the same manner as in Example 1, except that 29.2 parts by weight of the Compound (1) and 0.5 parts by weight of the electron accepting Compound (7a) below were used as the ETM instead of 29.7 parts by weight of the Compound (1).

(7a)

(10a)

Comparative Example 4

Example 4

An electrophotographic photoreceptor drum was prepared in the same manner as in Example 1, except that 29.2 parts by weight of the Compound (2) and 0.5 part by weight of the electron accepting Compound (7a) above were used as the ETM instead of 29.7 parts by weight of the Compound (1).

An electrophotographic photoreceptor drum was prepared in the same manner as in Example 1, except that 29.2 parts by weight of the dicyanofluorenone Compound (8a) above and 0.5 part by weight of the electron accepting Compound (7a) above were used as the ETM instead of 29.7 parts by weight of the Compound (1).

Comparative Example 1

An electrophotographic photoreceptor drum was prepared in the same manner as in Example 1, except that 29.7 parts by weight of dicyanofluorene Compound (8a) below was used as the ETM instead of the Compound (1).

Comparative Example 5

An electrophotographic photoreceptor drum was prepared in the same manner as in Example 1, except that 29.2 parts by weight of the naphthalenetetracarboxylic acid diimide derivative Compound (9a) above and 0.5 part by weight of the electron accepting Compound (7a) above were used as the ETM instead of 29.7 parts by weight of the Compound (1).

(8a)

Comparative Example 6

An electrophotographic photoreceptor drum was prepared in the same manner as in Example 1, except that 29.2 parts by weight of the naphthalenetetracarboxylic acid diimide derivative Compound (10a) above and 0.5 part by weight of the electron accepting Compound (7a) above were used as the ETM instead of 29.7 parts by weight of the Compound (1).

Experimental Example

Electrostatic properties of the respective electrophotographic photoreceptor prepared in the Examples and the Comparative Examples were evaluated using a corona-charging type drum photoreceptor evaluation apparatus manufactured by Samsung Electronics Co. The initial charge and exposure potentials and the charge and exposure potentials after 6,000 cycles were measured.

Comparative Example 2

An electrophotographic photoreceptor drum was prepared in the same manner as in Example 1, except that 29.7 parts by weight of the naphthalenetetracarboxylic acid diimide derivative of Compound (9a) below was used as the ETM instead of the Compound (1).

(9a)

The measured results are shown in Table 2.

TABLE 2

|  | Vo initial | Vd initial | Vo 6000 | Vd 6000 |
| --- | --- | --- | --- | --- |
| Example 1 | 980 | 78 | 950 | 82 |
| Example 2 | 990 | 75 | 965 | 80 |
| Example 3 | 990 | 100 | 990 | 105 |
| Example 4 | 980 | 100 | 975 | 103 |
| Comparative Example 1 | 680 | 73 | 450 | 79 |
| Comparative Example 2 | 920 | 82 | 815 | 97 |
| Comparative Example 3 | 945 | 79 | 880 | 86 |
| Comparative Example 4 | 915 | 98 | 840 | 110 |

Comparative Example 3

An electrophotographic photoreceptor drum was prepared in the same manner as in Example 1, except that 29.7 parts by weight of the naphthalenetetracarboxylic acid diimide derivative of Compound (10a) below was used as the ETM instead of the Compound (1).

TABLE 2-continued

|  | Vo initial | Vd initial | Vo 6000 | Vd 6000 |
|---|---|---|---|---|
| Comparative Example 5 | 950 | 105 | 835 | 111 |
| Comparative Example 6 | 970 | 101 | 895 | 104 |

Vo initial: initial charge potential
Vd initial: initial exposure potential
Vo 6000: charge potential after 6000 cycles
Vd 6000: exposure potential after 6000 cycles Referring to Table 2, in the case of Examples 1 and 2 using the Compounds (1) and (2), which are the naphthalenetetracarboxylic acid diimide derivatives according to the present invention, as an ETM, the charge potentials after 6000 cycles are only 25-30 V lower than the initial charge potentials, indicating that the stability of charging potential is good. In the case of Example 3 and 4 using a small amount of the electron accepting Compound (7a) in combination with the Compound (1) or (2), respectively, the stability of charging potential is even better than those of Examples 1 and 2.

In the case of Comparative Examples 1 and 4 using the dicyanofluorene ETM, the charging potentials are lower than those of Examples 1-4 regardless of the inclusion of the electron accepting compound and the stability of the charging potential is very poor.

In the case of Comparative Examples 2, 3, 5, and 6 in which the naphthalenetetracarboxylic acid diimide compound having lower solubility in organic solvents than the naphthalenetetracarboxylic acid diimide compound according to the present invention, the charging potentials are lower than those of Examples 1-4 regardless of the inclusion of the electron accepting compound and the stability of the charging potential is very poor.

Thus, the photoreceptor containing the naphthalenetetracarboxylic acid diimide derivatives according to the present invention has better electrostatic properties than the photoreceptor containing the conventional naphthalenetetracarboxylic acid derivative or dicyanofluorene compound as the ETMs. This is because the naphthalenetetracarboxylic acid diimide derivative according to the present invention has higher solubility in organic solvents such as methylene chloride and 1,1,2-trichloroethane, and improved compatibility with polyester binder resins, and thus has better electron transporting ability.

As described above, the electrophotographic photoreceptor containing the naphthalenetetracarboxylic acid diimide derivative according to the present invention has high solubility in organic solvents and improved compatibility with binder resins, thus providing improved electron transporting ability.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An electrophotographic photoreceptor comprising an electrically conductive substrate and a photosensitive layer formed thereon, the photosensitive layer comprising a naphthalenetetracarboxylic acid diimide derivative of Formula (1):

(1)

wherein $R_1$ and $R_2$ are independently selected from the group consisting of a hydrogen atom, a halogen atom, a $C_1$-$C_{20}$ substituted or unsubstituted alkyl group, and a $C_1$-$C_{20}$ substituted or unsubstituted alkoxy group;
$R_3$ is selected from the group consisting of a $C_1$-$C_{20}$ substituted or unsubstituted alkyl group, a $C_1$-$C_{20}$ substituted or unsubstituted alkoxy group, a $C_7$-$C_{30}$ substituted or unsubstituted aralkyl group, and a group having the formula —$(CH_2)_n$—Y—$R_4$;
Ar is a $C_6$-$C_{30}$ substituted or unsubstituted aryl group;
Y is an oxygen or sulfur atom;
$R_4$ is a hydrogen atom or a $C_1$-$C_{20}$ substituted or unsubstituted alkyl group; and
n is an integer between 1 and 12.

2. The electrophotographic photoreceptor of claim 1, wherein $R_1$ and $R_2$ are a hydrogen atom, $R_3$ is selected from the group consisting of methyl, ethyl, propyl, butyl, pentyl, benzyl, or methylbenzyl, and Ar is selected from the group consisting of phenyl, nitrophenyl, hydroxyphenyl, halophenyl, methoxyphenyl, methylphenyl, naphthyl, anthracenyl, and phenanthrenyl.

3. An electrophotographic imaging apparatus comprising an electrophotographic photoreceptor, wherein the electrophotographic photoreceptor comprises an electrically conductive substrate and a photosensitive layer formed thereon, the photosensitive layer comprising a naphthalenetetracarboxylic acid diimide derivative having Formula (1) below:

(1)

wherein $R_1$ and $R_2$ are independently selected from the group consisting of a hydrogen atom, a halogen atom, a $C_1$-$C_{20}$ substituted or unsubstituted alkyl group, and a $C_1$-$C_{20}$ substituted or unsubstituted alkoxy group;
$R_3$ is selected from the group consisting of a $C_1$-$C_{20}$ substituted or unsubstituted alkyl group, a $C_1$-$C_{20}$ substituted or unsubstituted alkoxy group, a $C_7$-$C_{30}$ substituted or unsubstituted aralkyl group, and a group having the formula —$(CH_2)_n$—Y—$R_4$;
Ar is a $C_6$-$C_{30}$ substituted or unsubstituted aryl group;
Y is an oxygen or sulfur atom;
$R_4$ is a hydrogen atom or a $C_1$-$C_{20}$ substituted or unsubstituted alkyl group; and
n is an integer between 1 and 12.

4. The electrophotographic imaging apparatus of claim 3, wherein $R_1$ and $R_2$ are a hydrogen atom, $R_3$ is selected from the group consisting of methyl, ethyl, propyl, butyl, pentyl, benzyl, or methylbenzyl, and Ar is selected from the group consisting of phenyl, nitrophenyl, hydroxyphenyl, halophenyl, methoxyphenyl, methylphenyl, naphthyl, anthracenyl, and phenanthrenyl.

5. An electrophotographic cartridge comprising:
an electrophotographic photoreceptor comprising an electrically conductive substrate and a photosensitive layer formed thereon, the photosensitive layer comprising a naphthalenetetracarboxylic acid diimide derivative of Formula (1) below; and
at least one of a charging device charging the electrophotographic photoreceptor, a developing device developing an electrostatic latent image formed on the electrophotographic photoreceptor, and a cleaning device cleaning a surface of the electrophotographic photoreceptor,
wherein the electrophotographic cartridge being attachable to or detachable from an image forming apparatus, (1)

wherein $R_1$ and $R_2$ are independently selected from the group consisting of a hydrogen atom, a halogen atom, a $C_1$-$C_{20}$ substituted or unsubstituted alkyl group, and a $C_1$-$C_{20}$ substituted or unsubstituted alkoxy group;
$R_3$ is selected from the group consisting of a $C_1$-$C_{20}$ substituted or unsubstituted alkyl group, a $C_1$-$C_{20}$ substituted or unsubstituted alkoxy group, a $C_7$-$C_{30}$ substituted or unsubstituted aralkyl group, and a group having the formula —$(CH_2)_n$—Y—$R_4$;
Ar is a $C_6$-$C_{30}$ substituted or unsubstituted aryl group;
Y is an oxygen or sulfur atom;
$R_4$ is a hydrogen atom or a $C_1$-$C_{20}$ substituted or unsubstituted alkyl group; and
n is an integer between 1 and 12.

6. The electrophotographic cartridge of claim 5, wherein $R_1$ and $R_2$ are a hydrogen atom, $R_3$ is selected from the group consisting of methyl, ethyl, propyl, butyl, pentyl, benzyl, or methylbenzyl, and Ar is selected from the group consisting of phenyl, nitrophenyl, hydroxyphenyl, halophenyl, methoxyphenyl, methylphenyl, naphthyl, anthracenyl, and phenanthrenyl.

7. An electrophotographic photoreceptor drum comprising:
a drum attachable to and detachable from an image forming apparatus; and
an electrophotographic photoreceptor disposed on the drum, wherein the electrophotographic photoreceptor comprises an electrically conductive substrate and a photosensitive layer formed thereon, the photosensitive layer comprising a naphthalenetetracarboxylic acid diimide derivative of Formula (1) below:

(1)

wherein $R_1$ and $R_2$ are independently selected from a group consisting of a hydrogen atom, a halogen atom, a $C_1$-$C_{20}$ substituted or unsubstituted alkyl group, and a $C_1$-$C_{20}$ substituted or unsubstituted alkoxy group;
$R_3$ is selected from a group consisting of a $C_1$-$C_{20}$ substituted or unsubstituted alkyl group, a $C_1$-$C_{20}$ substituted or unsubstituted alkoxy group, a $C_7$-$C_{30}$ substituted and unsubstituted aralkyl group, or a group having the formula —$(CH_2)_n$—Y—$R_4$;
Ar is a $C_6$-$C_{30}$ substituted or unsubstituted aryl group;
Y is an oxygen or sulfur atom;
$R_4$ is a hydrogen atom or a $C_1$-$C_{20}$ substituted or unsubstituted alkyl group; and
n is an integer between 1 and 12.

8. The electrophotographic photoreceptor drum of claim 7, wherein $R_1$ and $R_2$ are a hydrogen atom, $R_3$ is selected from a group consisting of methyl, ethyl, propyl, butyl, pentyl, benzyl, or methylbenzyl, and Ar is selected from a group consisting of phenyl, nitrophenyl, hydroxyphenyl, halophenyl, methoxyphenyl, methylphenyl, naphthyl, anthracenyl, or phenanthrenyl.

9. An image forming apparatus comprising:
a photoreceptor unit including an electrically conductive substrate and a photosensitive layer formed thereon, the photosensitive layer including a naphthalenetetracarboxylic acid diimide derivative of Formula (1) below;
a charging device for charging the photoreceptor unit;
an image-forming light irradiating device for irradiating light onto the charged photoreceptor unit to form an electrostatic latent image on the photoreceptor unit;
a developing unit for developing the electrostatic latent image with a toner to form a toner image on the photoreceptor unit; and
a transfer device for transferring the toner image onto a receiving material:

(1)

wherein $R_1$ and $R_2$ are independently selected from a group consisting of a hydrogen atom, a halogen atom, a $C_1$-$C_{20}$ substituted or unsubstituted alkyl group, or a $C_1$-$C_{20}$ substituted and unsubstituted alkoxy group;
$R_3$ is selected from a group consisting of a $C_1$-$C_{20}$ substituted or unsubstituted alkyl group, a $C_1$-$C_{20}$ substituted or unsubstituted alkoxy group, a $C_7$-$C_{30}$ substituted and unsubstituted aralkyl group, or a group having the formula —$(CH_2)_n$—Y—$R_4$;

Ar is a $C_6$-$C_{30}$ substituted or unsubstituted aryl group;

Y is an oxygen or sulfur atom;

$R_4$ is a hydrogen atom or a $C_1$-$C_{20}$ substituted or unsubstituted alkyl group; and n is an integer between 1 and 12.

* * * * *